United States Patent [19]

Mushika

[11] Patent Number: 4,794,910

[45] Date of Patent: Jan. 3, 1989

[54] MEDICAL APPLIANCE DRIVING APPARATUS

[75] Inventor: Sadahiko Mushika, Tokyo, Japan

[73] Assignee: Aisin Seiki Kabushiki Kaisha, Aichi, Japan

[21] Appl. No.: 67,042

[22] Filed: Jun. 29, 1987

[30] Foreign Application Priority Data

Jun. 28, 1986 [JP] Japan .................................. 61-152177

[51] Int. Cl.$^4$ .............................................. A61B 25/00
[52] U.S. Cl. ....................................................... 600/18
[58] Field of Search .................. 604/99; 128/1 D, 752

[56] References Cited

U.S. PATENT DOCUMENTS

| | | | |
|---|---|---|---|
| 3,452,738 | 7/1969 | Jones | 128/ |
| 3,465,746 | 9/1969 | Guarino | 128/ |
| 3,698,381 | 10/1972 | Federico et al. | 128/ |
| 4,162,543 | 7/1979 | Shunakov et al. | 128/1 D X |
| 4,323,071 | 4/1982 | Simpson et al. | 604/99 X |
| 4,332,254 | 6/1982 | Lundquist | 604/99 X |
| 4,361,152 | 11/1982 | Pate | 604/99 |
| 4,439,186 | 3/1984 | Kuhl | 604/99 |
| 4,546,760 | 10/1985 | Suzuki et al. | 128 ID/ |
| 4,548,550 | 10/1985 | Tsuji | 417/390 |
| 4,556,997 | 12/1985 | Takamiya et al. | 623/3 |
| 4,573,883 | 3/1986 | Noon et al. | 604/99 |
| 4,583,525 | 4/1986 | Suzuki et al. | 128/1 D |
| 4,648,385 | 3/1987 | Oumi et al. | 128 ID/ |
| 4,653,539 | 3/1987 | Bell | 604/99 X |
| 4,654,027 | 3/1987 | Drajan et al. | 604/99 |

Primary Examiner—Edward M. Coven
Attorney, Agent, or Firm—Sughrue, Mion, Zinn, Macpeak & Seas

[57] ABSTRACT

A medical appliance driving apparatus has pressure regulating control valves connected to positive and negative pressure sources and an isolator having an input chamber and an output chamber which are defined by a moveable membrane. The input chamber is connected to the pressure regulating control valves. An output valve is connected to the output chamber of the isolator, and a microcomputer is provided for switching the control valves to the positive pressure side or the negative pressure side and controlling the operation of the output valve. When the control valves are activated to provide positive pressure the output valve is opened, the positive pressure which is supplied to the input chamber causes the moveable membrane to move in a direction in which the medical appliance is inflated. After a predetermined period of time the output valve is closed to maintain the pressure supplied to the medical appliance as it is, and the control valves are switched to provide negative pressure to the input chamber of the isolator. Accordingly, the input side of the isolator can be communicated with the negative pressure source while the medical appliance is maintained in the inflated state. Thus it is possible to quickly switch the state of the medical appliance from inflation of deflation. A similar sequence is followed to change from deflation to inflation.

3 Claims, 4 Drawing Sheets

MEDICAL APPLIANCE DRIVING APPARATUS

BACKGROUND OF THE INVENTION

1. Field of the Invention

The present invention relates to a medical appliance driving apparatus designed to inflate and deflate a medical appliance such as an artificial heart pump or an intra-aortic balloon pump by alternatively supplying positive and negative pressures thereto. More particularly, the present invention pertains to an apparatus for driving an intra-aortic balloon pump.

2. Description of the Related Art

Medical appliance driving apparatus are required to increase the speed of inflation and deflation of the associated medical appliances. It is preferable, in order to meet such requirements, to have a sharp rise (or drop) of the pressure supplied to the medical appliances. For this reason, one type of driving apparatus employs an accumulator to prevent variations in pressure. However, it is necessary to considerably increase the capacity of the accumulator in order to absorb an increase or decrease in pressure produced in the accumulator when the state of the medical appliance is changed from inflation to deflation or vice versa. Accordingly, it is difficult to reduce the overall size of the driving apparatus.

There is another type of medical appliance driving apparatus wherein a solenoid valve is disposed in parallel to a pressure regulating valve and a pressure from a pressure source such as a compressor or a vacuum pump is directly supplied to the medical appliance by controlling the solenoid valve so as to be opened and closed at a predetermined timing, thereby providing compensation for the rise of pressure supplied to the medical appliance.

For example, a driving apparatus disclosed in Japanese Kokai No. 59-177062, published Oct. 6, 1984, is arranged such that, while a negative pressure is being supplied to a medical appliance, a positive pressure is directly supplied from a compressor through a solenoid valve and kept higher than a set pressure regulated by a pressure regulating valve to thereby compensate for the rise of pressure when a positive pressure is supplied to the medical appliance.

Driving apparatus disclosed in Japanese Kokai Nos. 59-206698, published Nov. 22, 1984, and 59-207158., published Nov. 24, 1984, respectively, are arranged such that, when a positive pressure is supplied to a medical appliance, a positive pressure from a compressor is directly supplied through a solenoid valve for a predetermined period of time to thereby compensate for the rise of pressure supplied to the medical appliance.

Driving apparatus disclosed in Japanese Kokai Nos. 59-206699, published Nov. 22, 1984, and 59-207158 are provided with an auxiliary accumulator for accumulating a positive pressure from a compressor in addition to an accumulator for accumulating a regulated pressure, and when the regulated pressure is supplied to the medical appliance, the pressure accumulated in the auxiliary accumulator is supplied together with said regulated pressure to thereby provide compensation for the rise of pressure supplied to the medical appliance.

A driving apparatus disclosed in Japanese Kokai No. 60-106462, published, June 11, 1985, is arranged such that, when a positive pressure is supplied to a medical appliance, a positive pressure from a compressor is directly supplied through a solenoid valve to thereby compensate for the rise of pressure supplied to the medical appliance, and when the pressure in the medical appliance reaches a predetermined value, the solenoid valve is closed.

In all of these driving apparatus a pressure from a pressure source is directly led to a medical appliance in order to compensate for the rise of pressure supplied to the medical appliance. Accordingly, when the medical appliance is to be inflated to a positive pressure fluid is needed to compensate for a negative pressure in the pipe line, whereas, when the medical appliance is to be deflated, a negative pressure fluid is needed to compensate for a positive pressure in the pipe line. For this reason, it has heretofore been unavoidable that the rise of pressure at the time of switching the state of the medical appliance from inflation to deflation and vice versa is somewhat slow.

SUMMARY OF THE INVENTION

In view of the above described circumstances, it is a primary object of the present invention to provide a medical appliance driving apparatus which is so designed that said rise of pressure is as steep as possible.

According to the present invention, there is provided a medical appliance driving apparatus comprising: switching valve means connected to both positive and negative pressure sources to output both positive and negative pressures; isolator means having an input chamber and an output chamber which are defined by a moveable membrane, the input chamber being connected to the switching valve means; valve means connected to the output chamber of the isolator means; and electronic control means for switching the switching valve means to the positive pressure side and opening the valve means to supply a positive pressure to the medical appliance and for closing the valve means after a predetermined time from the opening of the valve means, and further activating the switching valve means to the negative pressure source side.

According to this arrangement when the switching valve means is activated to the positive pressure source side and the valve means is opened, a positive pressure supplied to the input chamber causes the moveable membrane to move in a direction in which the medical appliance is inflated. When the predetermined time is over, the valve means is closed to maintain the pressure in the medical appliance at a constant level. Then, the switching valve means is switched to the negative pressure source side. In other words, the state of the medical appliance is judged on the basis of the opening time of the valve means.

The foregoing and other objects, features and advantages of the invention will be apparent from the following more particular description of a preferred embodiment of the invention as illustrated in the accompanying drawings.

DESCRIPTION OF THE PREFERRED EMBODIMENT

One embodiment of the present invention will be described hereinafter in detail with reference to the accompanying drawings.

Figure 1:
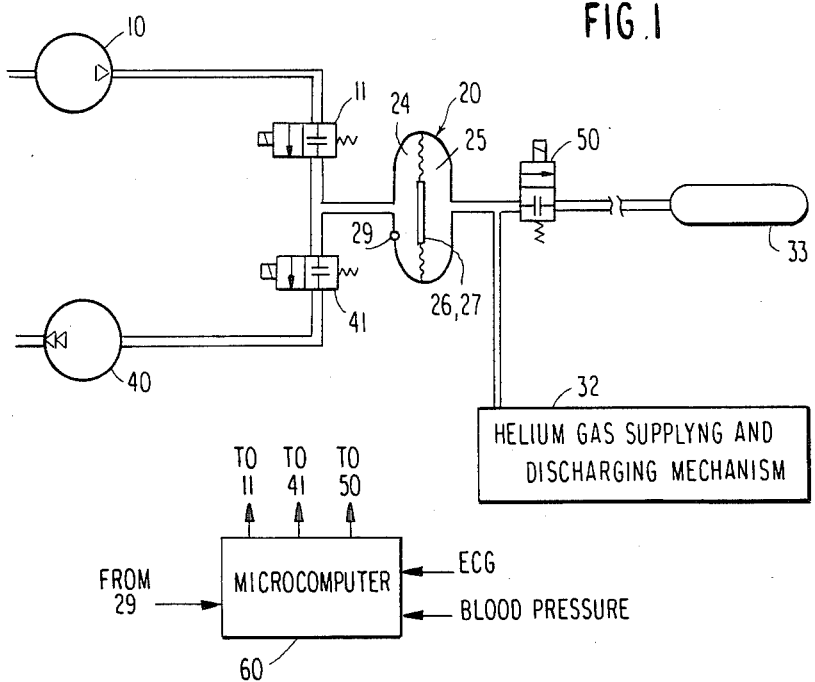
FIG. 1 is a block diagram of one embodiment of the medical appliance driving apparatus according to the present invention.

Referring first to FIG. 1, which is a block diagram of a medical appliance driving apparatus according to the present invention, the output side of a compressor 10, which serves as a positive pressure source, is connected to a pressure regulating valve 11 as a switching valve means, the output side of which is connected to an isolator 20 which serves as isolator means. The isolator 20 changes the medium for driving a medical appliance from air to a gas such as helium. Thus, the driving medium is made safe for living organisms.

Figure 2:
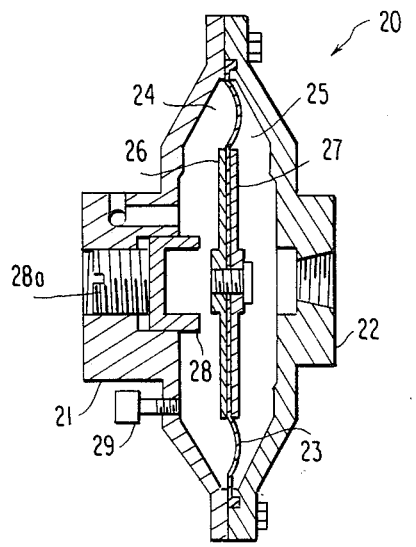
FIG. 2 is a sectional view of the isolator means shown in FIG. 1.

Referring next to FIG. 2, which shows the isolator 20 in detail, the interior of the isolator 20 is divided into an input chamber 24 and an output chamber 25 by means of a diaphragm 23 which is clamped between housing members 21 and 22. Plates 26 and 27 are secured to both sides, respectively, of the central portion of the diaphragm 23. The diaphragm 23 and the plates 26, 27 define in combination a moveable membrane. A limiting member 28 for limiting the amount of movement of the plate 26 is secured to the central portion of the housing 21. The limiting member 28 is in thread engagement with the housing 21 by means of a screw 28a. When turned, the limiting member 28 is moved sideways as viewed in the figure. When the limiting member 28 is moved leftward, the range within which the plates 26 and 27 can move is enlarged, whereas, when the limiting member 28 is moved rightward, said moveable range is decreased.

A pressure sensor 29 which serves as pressure detecting means is disposed on the side of the housing 21 which is closer to the input chamber 24.

Referring back to FIG. 1, the output chamber 25 of the isolator 20 is connected to a helium gas supplying a discharging mechanism 32 and a solenoid valve 50 which serves as a valve means. The output side of the solenoid valve 50 is connected to an intra-aortic balloon pump 33 which defines a medical appliance in this embodiment. The helium gas supplying and discharging mechanism 32 serves to maintain the pressure of helium gas within the isolator 20 and the balloon pump 33 at a constant level.

The output of a vacuum pump 40 which serves as a negative pressure source is connected to a pressure regulating valve 41 as a switching valve means, the output side of which is connected to the input chamber 24 of the isolator 20.

A microcomputer 60, which serves as electronic control means, is connected at the input side thereof to the pressure sensor 29, whereas the microcomputer 60 at the output side thereof is connected to the pressure regulating valves 11, 41 and the solenoid valve 50.

The operation of the microcomputer 60 will next be explained with reference to flow charts shown in FIGS. 3, 4, 5, 6, and 7.

Figure 3:
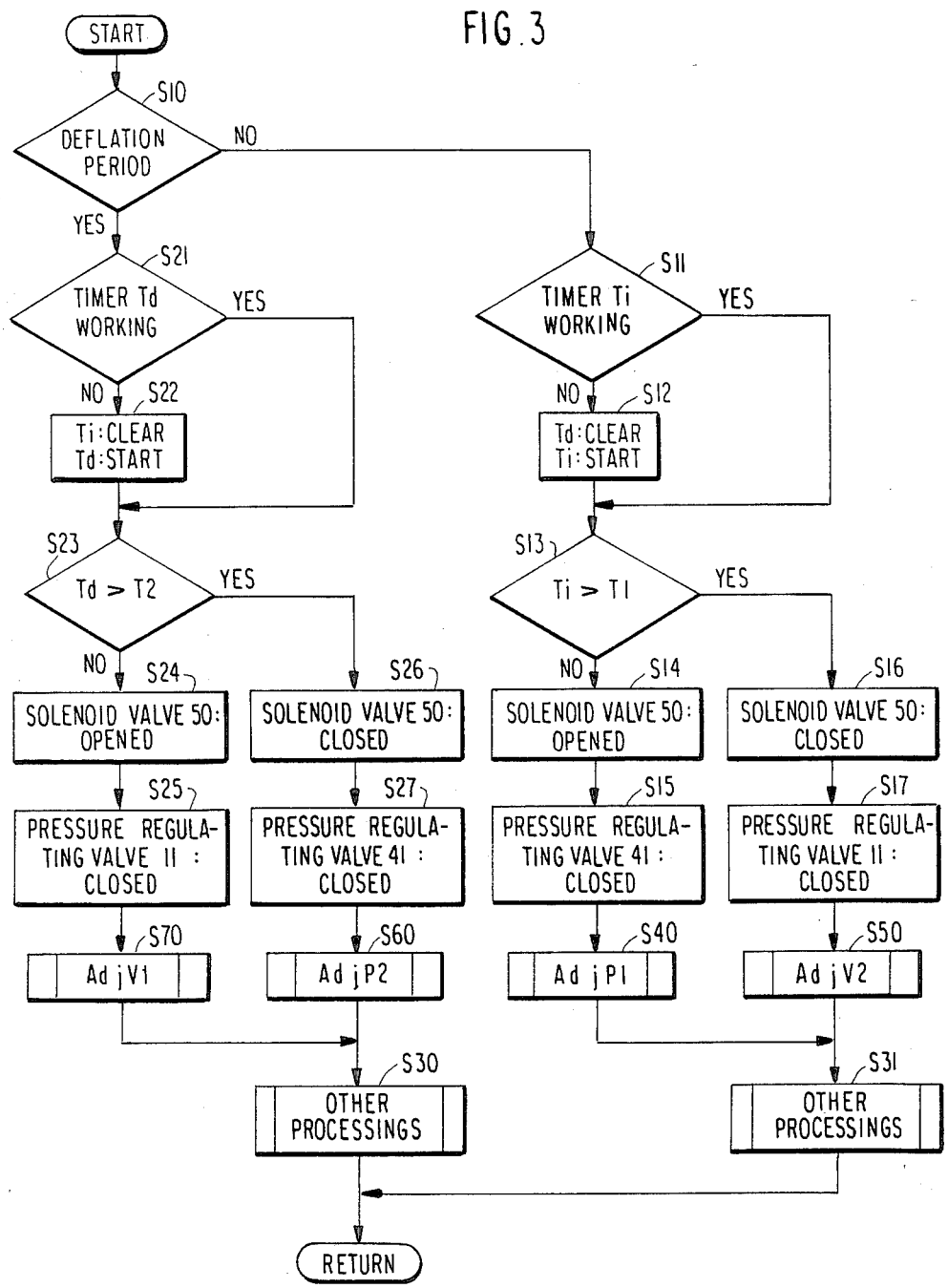
FIGS. 3, 4, 5, 6, and 7, are flow charts showing the operation of the embodiment.
Figure 4:
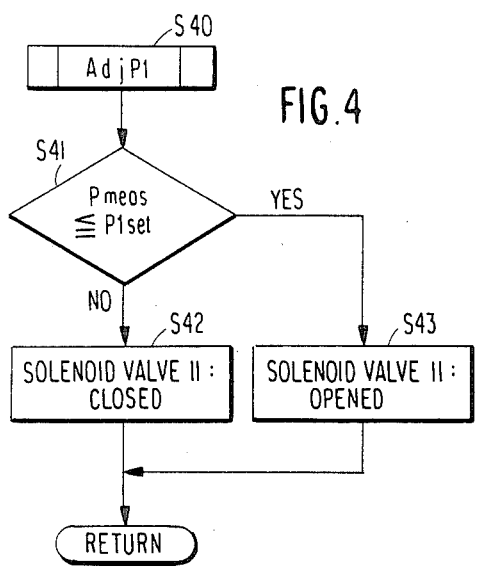
Figure 5:
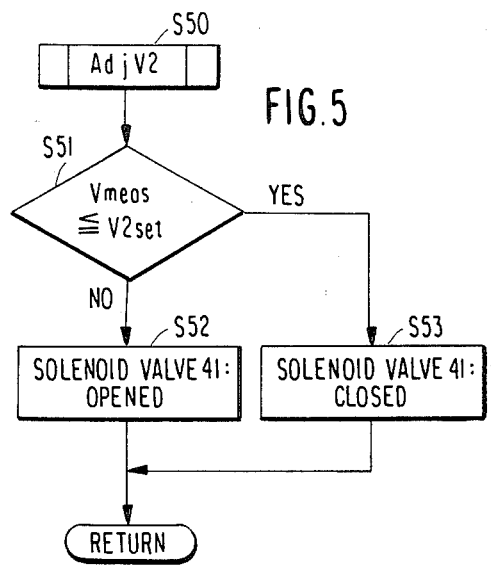
Figure 6:
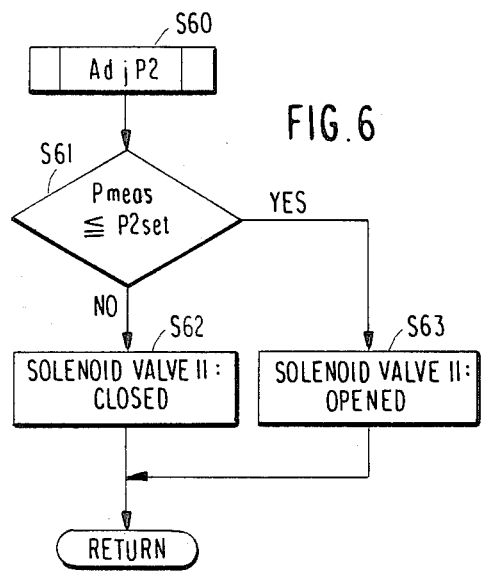
Figure 7:
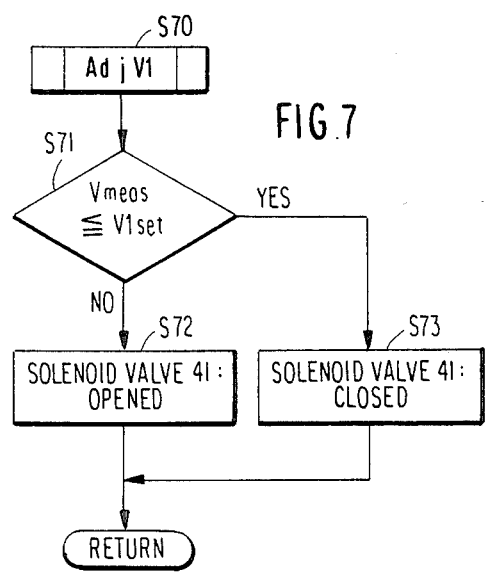
Figure 8:
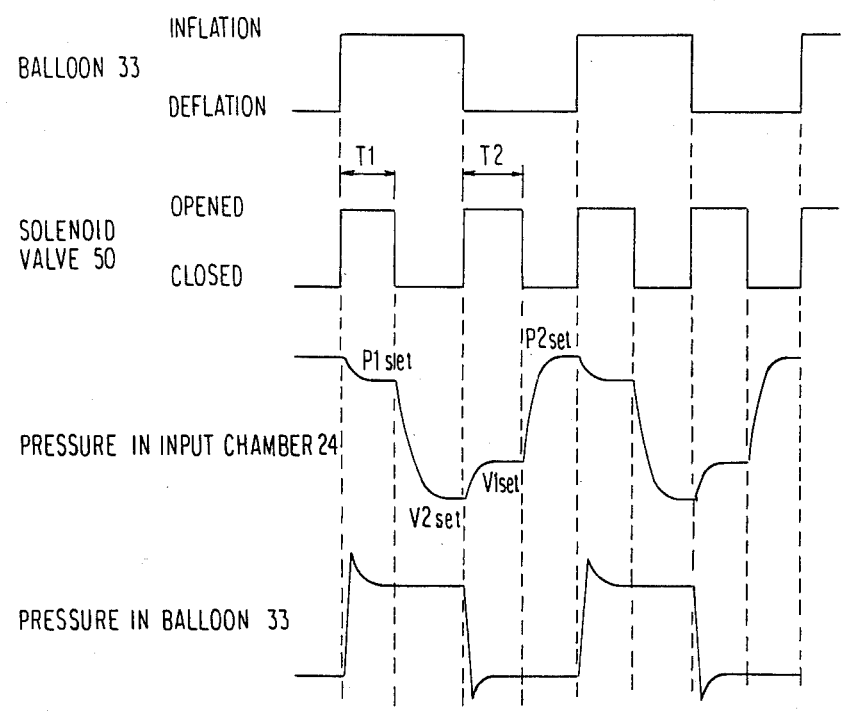
FIG. 8 is a timing chart showing the operation of the embodiment.

FIG. 3 shows the control functions which are executed according to the main routine. A judgement is made in Step S10 as to whether or not the balloon pump 33 is in the deflation period. The deflation period of the balloon pump 33 is determined as follows. For example, the microcomputer 60 is externally supplied with an electrocardiogram (ECG) signal and/or a blood pressure signal of a living organism under treatment to perform calculations in order to obtain deflation and inflation timing which is appropriate to a particular condition of the living organism on the basis of the input date. Description of the calculation and the like is omitted herein since it is not necessary to an understanding of the invention.

When the balloon pump 33 is judged to be in the inflation period in Step S10, positive pressure supply control which is shown in infra Step S11 is executed. In this control, a judgement is first made in Step S11 as to whether or not an inflation timer Ti is working. This timer Ti is started in Step S12 when it is judged in Step S11 that timer Ti is not working. Then the deflation timer Td is clear and the inflation timer Ti is started. In Step S11, when the timer Ti is working the process proceeds to Step S13. A judgement is made in Step S13, as to whether or not the timer Ti is over a predetermined time T1. Since, in this state, the timer Ti has just started, the process proceeds to Step S14, in which the solenoid valve 50 is opened to allow the output chamber 25 to communicate with the balloon pump 33.

At this time, the input chamber 24 of the isolator 20 has already been set to the set value P2set by opening the solenoid valve 11 as described later. In other words, the input chamber 24 is being supplied with a positive pressure and is thus pressurized. Accordingly, when the solenoid valve 50 is opened, the plate 27 is immediately moved in the direction for inflating the balloon pump 33, thereby starting inflation of the pump 33. It should be noted that Step S15 is executed in order to maintain the solenoid valve 41 in the closed position for safety.

At this time, positive pressure adjusting control AdjP1 shown in Step S40 is effected. This control is shown in the flow chart of FIG. 4. A judgement is made in Step S41 as to whether or not the pressure Pmeas represented by a value detected by the pressure sensor 29 disposed in the input chamber 24 of the isolator 20 is equal to or less than a set positive pressure valve P1set. When the pressure Pmeas is less than the set value P1set, the process proceeds to Step S43, in which the pressure regulating valve 11 is opened to introduce the pressure from the compressor 10 into valve the input chamber 24. When the pressure Pmeas reaches the set value P1set, the pressure regulating valve 11 is closed in Step S42.

Referring back to FIG. 3, other processings are executed in Step S31, and the process returns. When it is judged in Step S13 that the timer Ti is over the predetermined time T1 the process proceeds to Step S16, in which the solenoid valve 50 is closed to cut off the supply of positive pressure thereafter. Thus, the pressure in the balloon pump 33 is maintained as it is, so that the pump 33 is held in the inflated state. The solenoid valve 11 is closed in Step S17 to cut off the supply of positive pressure into the input chamber 24.

Then negative pressure adjusting control AdjV2 is carried out in Step S50. This control is executed in order to set a negative pressure required during the subsequent deflation period in the input chamber 24 while the balloon pump 33 is being inflated by means of the positive pressure. The negative pressure adjusting control AdjV2 will be explained below with reference to the flow chart shown in FIG. 5. A judgement is made in Step S51 as to whether or not the pressure Vmeas, represented by a value detected by the pressure sensor 29 disposed in the input chamber 24 is equal to or less than a set negative pressure value V2set. When the pressure Vmeas is greater than the set value V2set, the pressure regulating valve 41 is opened in Step S52 to introduce the pressure from the vacuum pump 40 into the input chamber 24. When the pressure Vmeas reaches the set value V2set, the pressure regulating valve 41 is closed in Step 53.

The control executed during the deflation period will next be explained with reference to FIG. 3.

When it is judged in Step S10 that the balloon pump 33 is during the deflation period, negative pressure supply control shown in infra Step S21 is executed. In this control, a judgement is first made in Step S21 as to whether or not a deflation timer Td is working. This timer Td is started in Step S22 when it is judged in Step S21 that the timer is not working. Then the inflation timer Ti is clear and the deflation timer Td is started.

In Step S21 when the timer Td is working the process proceeds to Step 23. A judgement is made in Step 23, as to whether or not the timer Td is over the predetermined time T2. Since, in this state, the timer Td has just started, the process proceeds to Step S24, in which the solenoid valve 50 is opened to allow the output chamber 25 to communicate with the balloon pump 33. At this time, the input chamber 24 of the isolator 20 has already been set to the set value V2set as described above. In other words, the input chamber 24 is connected with the negative pressure source and is pressurized accordingly. When the solenoid valve 50 is opened, the plate 27 is immediately moved in a direction for deflating the balloon pump 33 thereby starting deflation of the pump 33. It should be noted that Step S25 is executed in order to maintain the solenoid valve 11 in the closed position.

At this time, negative pressure adjusting control AdjV1 shown in Step S70 is effected. This control is shown in the flow chart of FIG. 7. A judgement in Step S71 as to whether or not the input pressure Vmeas represented by a value detected by the pressure sensor 29 disposed in the input chamber 24 is equal to or less than a set negative pressure value V1set. When the pressure Vmeas is greater than the set value V1set, the process proceeds to Step S72, in which the pressure regulating valve 41 is opened to introduce the pressure from the vacuum pump 40 into the input chamber 24. When the pressure Vmeas reaches the set value V1set, the pressure regulating valve 41 is closed in Step S73.

Referring back to FIG. 3, other processings are executed in Step S30, and the process returns. When it is judged in Step S23 that the timer Td is over the predetermined time T2 the process proceeds to Step S26, in which the solenoid valve 50 is closed to cut off the supply of negative pressure thereafter. Thus, the pressure in the balloon pump 33 is maintained as it is, so that the pump 33 is held in the deflated state. The solenoid valve 41 is closed in Step S27 to cut off the supply of negative pressure for the input chamber 24.

After these processings, the pressure inside the input chamber 24 is set to a set value P2set for the subsequent inflation period in Step S60. This control is effected in order to set a positive pressure required during the subsequent inflation period in the input chamber 24 while the balloon pump 33 is held in the deflated state. This control process will be explained below with reference to the flow chart shown in FIG. 6. A judgement is made in Step S61 as to whether or not the input pressure Pmeas represented by a value detected by the pressure sensor 29 disposed on the input chamber 24 is equal to or less than a set positive pressure value P2set. When the pressure Pmeas is less than the set value P2set, the pressure regulating valve 11 is opened in Step S62 to introduce an excessively high pressure from the compressor to the input chamber 24, the internal pressure of the input chamber 24 is adjusted at the set positive pressure value P1set (e.g., 200 mmHg).

When the balloon pump 33 is sufficiently inflated, that is, when the timer Ti is over the predetermined time T1 (e.g., 80 msec) during the inflation period, the solenoid valve 50 is closed to hold the balloon pump 33 in the inflated state until the subsequent contraction of the pump 33 begins. With the solenoid valves 11 and 41 closed and opened, respectively, the pressure inside the input chamber 24 is set in advance at the pressure value V2set (e.g., -200 mmHg) required at the beginning of the subsequent deflation period.

Before the deflation period begins, the solenoid valve 50 is closed and the balloon pump 33 is therefore held in the inflated state. At this time, the pressure inside the input chamber 24 is set at the negative pressure value V2set (e.g., 200 mmHg) by means of the solenoid valve 51. Then 27 is moved in a direction in which the balloon pump 33 is deflated. At this time, in order to prevent application of an excessively high pressure to the inside of the balloon pump 33, the pressure inside the input chamber 24 is set at the set negative pressure value V1set (e.g., -50 mmHg).

When the balloon pump 33 is sufficiently deflated, that is, when the timer Td reaches the predetermined time T2 (e.g., 80 msec) during the deflation period, the solenoid valve 50 is closed to hold the balloon pump 33 in the deflated state until the subsequent inflation of the pump 33 begins. With the solenoid valves 11 and 41 opened and closed, respectively, the pressure inside the input chamber 24 is set in advance at the pressure value P2set (e.g., 400 mmHg) required at the beginning of the subsequent inflation period.

It should be noted that the relationship between the various set values is as follows.

Set positive pressure values:

$$0 < P1set < P2set$$

Set negative pressure values:

$$V2set < V1set < 0.$$

As has been described above, it is possible according to the present invention to allow the input chamber of the isolator means to communicate with the negative pressure source while maintaining the medical appliance in the inflated state. Therefore, when the medial appliance is supplied with a negative pressure during the subsequent deflation period by opening the valve means, the input chamber of the isolator means has already been supplied with the required relative pressure. Accordingly, it is possible to eliminate the effect of resistance generated in the pipe line extending from the negative pressure source to the isolator means, and the input chamber of the isolator means can be pressurized in advance, so that it is possible to quickly switch the state of the medical appliance from inflation to deflation.

During the deflation period of the medical appliance, the input chamber of the isolator means can be communicated with the positive pressure source while the medical appliance is held in the deflated state. Therefore, when the medical appliance is supplied with a positive pressure in the subsequent inflation period by opening the valve means, the input chamber of the isolator means has already been supplied with the required positive pressure. Accordingly, it is possible to eliminate the effect of resistance generated in the pipe line which extends from the positive pressure source to the isolator means, and the input chamber of the isolator means can be pressurized in advance, so that it is possible to quickly switch the state of the medical appliance from deflation to inflation.

Further, since the pressure inside the input chamber compensates the consumption of the pressure at switching the state of the medical appliance from inflation to deflation, only the pressure regulating valve could respond to the pressure variations. Therefore, this embodiment does not require a tank.

While the invention has been particularly shown and described with reference to preferred embodiments thereof it will be understood by those in the art that the foregoing and other changes in form and details may be made therein without departing from the spirit and scope of the invention.

What is claimed is:

1. A medical appliance driving apparatus comprising:
   positive pressure supply means for supplying a positive pressure;
   negative pressure supply means for supplying a negative pressure;
   isolator means having an input chamber and an output chamber which are defined by a moveable membrane;
   positive pressure regulating valve means connected between said positive pressure supply means and said input chamber for selectively connecting said positive pressure supply means to said input chamber;
   negative pressure regulating valve means connected between said negative pressure supply means and said input chamber for selectively connecting said negative pressure supply means to said input chamber;
   output valve means connected to said output chamber of said isolator means;
   pressure detecting means for detecting the pressure in said input chamber of said isolator means;
   a medical appliance connected to the output side of said output valve means; and
   electronic control means for operating said pressure regulating valve means to selectively connect one of said supply means to said isolator means and for controlling the operation of said output valve means,
   wherein said electronic control means operates to open and close said positive pressure regulating valve means in response to the pressure detected in said input chamber by said pressure detecting means to maintain a first predetermined pressure value in said input chamber when said output valve means and said negative pressure regulating valve means are closed, to open said output valve means to supply a positive pressure to said medical appliance and after a predetermined time from the opening of said output valve means closes said output valve means to maintain the positive pressure supplied to said medical appliance, to close said positive pressure regulating valve means, to open and close said negative pressure regulating valve means in response to pressure detected in said input chamber by said pressure detecting means to maintain a second predetermined pressure in said input chamber, to open said output valve means to supply a negative pressure to said medical appliance and after a predetermined time from the opening of said output valve means to close said output valve means, to maintain the negative pressure supplied to said medical appliance and to continuously repeat the foregoing cycle.

2. An apparatus according to claim 1 wherein said medical appliance is a balloon pump.

3. An apparatus according to claim 2 further comprising additional supply means for supplying and discharging helium gas, said additional supply means being connected between said output chamber of said isolator means and the input side of said valve means.

* * * * *